(12) United States Patent
Sevenster (10) Patent No.: US 11,031,137 B2
(45) Date of Patent: Jun. 8, 2021

(54) HANDLING UNDETERMINED QUANTIFIABLE TARGET LESIONS WHILE TRACKING CANCEROUS LESIONS USING LONG AXIS AND SHORT AXIS MEAUSREMENT CONSISTENT WITH RESPONSE EVALUATION CRITERIA IN SOLID TUMORS (RECIST) GUIDELINES

(71) Applicant: KONINKLIJKE PHILIPS N.V., Eindhoven (NL)

(72) Inventor: Merlijn Sevenster, Chicago, IL (US)

(73) Assignee: Koninklijke Philips N.V., Eindhoven (NL)

( * ) Notice: Subject to any disclaimer, the term of this patent is extended or adjusted under 35 U.S.C. 154(b) by 463 days.

(21) Appl. No.: 15/503,844

(22) PCT Filed: Aug. 17, 2015

(86) PCT No.: PCT/IB2015/056239
§ 371 (c)(1),
(2) Date: Feb. 14, 2017

(87) PCT Pub. No.: WO2016/030792
PCT Pub. Date: Mar. 3, 2016

(65) Prior Publication Data
US 2017/0231592 A1 Aug. 17, 2017

Related U.S. Application Data

(60) Provisional application No. 62/043,440, filed on Aug. 29, 2014.

(51) Int. Cl.
*G16H 50/30* (2018.01)
*G16H 30/40* (2018.01)
(Continued)

(52) U.S. Cl.
CPC .............. *G16H 50/70* (2018.01); *A61B 5/055* (2013.01); *A61B 5/418* (2013.01); *A61B 6/032* (2013.01);
(Continued)

(58) Field of Classification Search
CPC ..... A61B 6/5217; A61B 5/055; A61B 6/5205; A61B 6/50; A61B 5/418; A61B 6/032;
(Continued)

(56) References Cited

U.S. PATENT DOCUMENTS

| 8,229,200 B2 | 7/2012 | Piacsek et al. |
| 2008/0027305 A1 | 1/2008 | Gundel |

(Continued)

FOREIGN PATENT DOCUMENTS

| EP | 2228451 A1 | 9/2010 |
| JP | 2010035634 A | 2/2010 |

OTHER PUBLICATIONS

Philips Healthcare: Multi Modality Tumor Tracking, Nov. 20, 2013.
(Continued)

*Primary Examiner* — Serkan Akar
*Assistant Examiner* — Aminah Asghar (57) ABSTRACT

A lesion tracking system (10) includes a data interface (12), a computation engine (18), and a visualization engine (26). The data interface (12) is configured to receive an identification (44) and measurements (56) of at least one target lesion (42), which includes at least one undetermined target lesion (52) according to a plurality of determined categories (54), and each undetermined target lesion (52) is quantified differently according to each of the plurality of determined categories (54). The computation engine (18) is configured to compute a range of quantified measurements according to each determined category for each undetermined target lesion (52), and to compute a quantified total range (70) for
(Continued)

| Lesion dashboard | | | | | | | | | |
|---|---|---|---|---|---|---|---|---|---|
| Alert: Progress on 5/1/2011 for Soft tissue lesion axis if resolved as tumor | | | | | | | | | |
| | | | | Cycle 1 - 1/1/2011 | | Cycle 2 - 3/1/2011 | | Cycle 3 - 5/1/2011 | |
| Description | Target lesion? | Category | | Long axis | Short axis | Long axis | Short axis | Long axis | Short axis |
| Soft tissue lesion | Y | Undetermined | | 3.1 | 3.1 | 3.5 | 3.1 | 4.8 | 3.1 |
| Pathological nodule | Y | Undetermined | | 2.1 | 1.9 | 2.1 | 1.8 | 2.1 | 1.9 |
| Liver mass | Y | Tumor | | 3.4 | 2.8 | 3.6 | 3 | 3.8 | 3.2 |
| Left hilar lymph node | Y | Lymph node | | 1.6 | 1.1 | 1.8 | 1.3 | 1.8 | 1.4 |
| | | SUM RANGE | | 9.5 – 9.7 | | 9.8 – 10.5 | | 10.2 – 12.1 | |
| | | NADIR RANGE | | | | 9.5 – 9.7 | | 9.5 – 9.7 | |
| | | RESPONSE RANGE | | | | 3.16 – 8.25 % | | 7.22 – 25.26 % | | the at least one target lesion based on a quantified measurement (62) for each determined target lesion and the computed range for each of the at least one undetermined target lesion. The visualization engine (26) is configured to generate a human readable display of the computed quantified total range (70) for the at least one target lesion.

11 Claims, 5 Drawing Sheets

(51) Int. Cl.
*A61B 5/00* (2006.01)
*G16H 50/70* (2018.01)
*A61B 5/055* (2006.01)
*A61B 6/03* (2006.01)
*A61B 6/00* (2006.01)
*G16H 10/20* (2018.01)

(52) U.S. Cl.
CPC ............ *A61B 6/461* (2013.01); *A61B 6/50* (2013.01); *A61B 6/5205* (2013.01); *A61B 6/5217* (2013.01); *G16H 30/40* (2018.01); *G16H 50/30* (2018.01); *G16H 10/20* (2018.01)

(58) Field of Classification Search
CPC ....... A61B 6/461; G06F 19/00; G06F 19/321; G16H 50/30; G16H 10/20; G16H 30/00–40; G16Z 99/00
See application file for complete search history.

(56) References Cited

U.S. PATENT DOCUMENTS

| | | |
|---|---|---|
| 2010/0303714 A1 | 12/2010 | Kirn |
| 2012/0033863 A1* | 2/2012 | Wojton ................ A61B 5/0013 382/128 |
| 2012/0130223 A1 | 5/2012 | Reicher |
| 2012/0134550 A1 | 5/2012 | Knoplioch et al. |
| 2013/0243244 A1 | 9/2013 | Miyamoto et al. |
| 2014/0038197 A1 | 2/2014 | Waldman et al. |
| 2015/0015612 A1* | 1/2015 | Kurosaki ............... G16H 15/00 345/636 |

OTHER PUBLICATIONS

Tirkes, T. et al., "Response Criteria in Oncologic Imaging: Review of Traditional and New Criteria", Radiographics, vol. 33, No. 5, Sep. 1, 2013, pp. 1323-1341.

Wahl, R, et al., "From RECIST to PERCIST: Evolving Considerations for PET Response Criteria in Solid Tumors", The Journal of Nuclear Medicine, vol. 50, No. 5 (Suppl), May 2009.

Edeline, J. et al., "Comparison of tumor response by response evaluation criteria in solid tumors (RECIST) and modified RECIST in patients treated with sorafenib for hepatocellular carcinoma", Cancer, vol. 118, Issue 1, Jan. 1, 2012, p. 147-156.

Nishino, M. et al., "Revised RECIST guideline version 1.1: What oncologists want to know and what radiologists need to know", American Journal of Roentagenology, 2010: 195: 281-289.

Rubin, D.L. et al., "automated tracking of quantitative assessments of tumor burden in clinical trials", Translational Oncology, Feb. 2014, 7(1): 23-35.

Serique, K.A. et al., "Using the semantic web and web apps to connect radiologists and oncologists", Enabling Technologies: Infrastructure for Collaborative Enterprises (WETICE), 2012 IEEE 21st International Workshop on Jun. 25-27, 2012, pp. 460-485.

Abajian, A. et al., "Informatics in radiology: improving clinical work flow through an AIM database: a sample web-based lesion tracking application", Radiographics, vol. 32, Issue 5, Sep.-Oct. 2012.

* cited by examiner

| 76 | 78 | | Cycle 1 - 1/1/2011 ~58 | ~60 | Cycle 2 - 3/1/2011 ~58 | ~60 | Cycle 3 - 5/1/2011 ~58 | ~60 |
|---|---|---|---|---|---|---|---|---|
| | Target lesion? | Category | Long axis | Short axis | Long axis | Short axis | Long axis | Short axis |
| Soft tissue lesion | Y | Lymph node | 3.1 | 3.1 | 3.5 | 3.1 | 4.8 | 3.1 |
| Pathological nodule | Y | Tumor | 2.1 | 1.9 | 2.1 | 1.8 | 2.1 | 1.9 |
| Liver mass | Y | Tumor | 3.4 | 2.8 | 3.6 | 3 | 3.8 | 3.2 |
| Left hilar lymph node | Y | Lymph node | 1.6 | 1.1 | 1.8 | 1.3 | 1.8 | 1.4 |
| | | SUM ~80 | 9.7 | | 10.1 | | 10.4 | |
| | | NADIR ~82 | | | 9.7 | | 9.7 | |
| | | RESPONSE ~84 | | | 4.12 % | | 7.22 % | |

FIG. 3A

| 76 | 78 | | Cycle 1 - 1/1/2011 ~58 | ~60 | Cycle 2 - 3/1/2011 ~58 | ~60 | Cycle 3 - 5/1/2011 ~58 | ~60 |
|---|---|---|---|---|---|---|---|---|
| | Target lesion? | Category | Long axis | Short axis | Long axis | Short axis | Long axis | Short axis |
| Soft tissue lesion | Y | Lymph node | 3.1 | 3.1 | 3.5 | 3.1 | 4.8 | 3.1 |
| Pathological nodule | Y | Lymph node | 2.1 | 1.9 | 2.1 | 1.8 | 2.1 | 1.9 |
| Liver mass | Y | Tumor | 3.4 | 2.8 | 3.6 | 3 | 3.8 | 3.2 |
| Left hilar lymph node | Y | Lymph node | 1.6 | 1.1 | 1.8 | 1.3 | 1.8 | 1.4 |
| | | SUM ~80 | 9.5 | | 9.8 | | 10.2 | |
| | | NADIR ~82 | | | 9.5 | | 9.5 | |
| | | RESPONSE ~84 | | | 3.16 % | | 7.37 % | |

FIG. 3B

| 76 | 78 | | Cycle 1 - 1/1/2011 | | Cycle 2 - 3/1/2011 | | Cycle 3 - 5/1/2011 | |
|---|---|---|---|---|---|---|---|---|
| | Target lesion? | Category | Long axis | Short axis | Long axis | Short axis | Long axis | Short axis |
| Soft tissue lesion | Y | Tumor | 3.1 | 3.1 | 3.5 | 3.1 | 4.8 | 3.1 |
| Pathological nodule | Y | Tumor | 2.1 | 1.9 | 2.1 | 1.8 | 2.1 | 1.9 |
| Liver mass | Y | Tumor | 3.4 | 2.8 | 3.6 | 3 | 3.8 | 3.2 |
| Left hilar lymph node | Y | Lymph node | 1.6 | 1.1 | 1.8 | 1.3 | 1.8 | 1.4 |
| | | SUM — 80 | 9.7 | | 10.1 | | 12.1 | |
| | | NADIR — 82 | | | 9.7 | | 9.7 | |
| | | RESPONSE — 84 | | | 8.25 % | | 24.74 % | |

FIG. 3C

| 76 | 78 | | Cycle 1 - 1/1/2011 | | Cycle 2 - 3/1/2011 | | Cycle 3 - 5/1/2011 | |
|---|---|---|---|---|---|---|---|---|
| | Target lesion? | Category | Long axis | Short axis | Long axis | Short axis | Long axis | Short axis |
| Soft tissue lesion | Y | Tumor | 3.1 | 3.1 | 3.5 | 3.1 | 4.8 | 3.1 |
| Pathological nodule | Y | Lymph node | 2.1 | 1.9 | 2.1 | 1.8 | 2.1 | 1.9 |
| Liver mass | Y | Tumor | 3.4 | 2.8 | 3.6 | 3 | 3.8 | 3.2 |
| Left hilar lymph node | Y | Lymph node | 1.6 | 1.1 | 1.8 | 1.3 | 1.8 | 1.4 |
| | | SUM — 80 | 9.5 | | 10.2 | | 11.9 | |
| | | NADIR — 82 | | | 9.5 | | 9.5 | |
| | | RESPONSE — 84 | | | 7.37 % | | 25.26 % | |

HANDLING UNDETERMINED QUANTIFIABLE TARGET LESIONS WHILE TRACKING CANCEROUS LESIONS USING LONG AXIS AND SHORT AXIS MEAUSREMENT CONSISTENT WITH RESPONSE EVALUATION CRITERIA IN SOLID TUMORS (RECIST) GUIDELINES

CROSS-REFERENCE TO PRIOR APPLICATIONS

This application is the U.S. National Phase application under 35 U.S.C. § 371 of International Application No. PCT/IB2015/056239, filed on Aug. 17, 2015, which claims the benefit of U.S. Provisional Application No. 62/043,440, filed on Aug. 29, 2014. These applications are hereby incorporated by reference herein.

The following relates generally to medical informatics. It finds particular application in conjunction with measuring and reporting of cancerous lesions, and will be described with particular reference thereto. However, it will be understood that it also finds application in other usage scenarios and is not necessarily limited to the aforementioned application.

Response Evaluation Criteria In Solid Tumors (RECIST) guidelines are the dominant guidelines used to track cancerous lesions. The RECIST guidelines are the result of an international collaboration to standardize and quantify measurement of cancerous tumors in response to previous subjective measuring of responses to treatments. Quantification and standardization is important to evaluate the effectiveness of methods of cancer treatment for individual patients and as part of clinical trials.

RECIST guidelines distinguish between target and non-target lesions, and further distinguish target lesions between enlarged lymph nodes and malignant neoplasms, e.g. tumors. Tumors above a specified size are tracked and measured for each organ in an image slice, typically an X-ray Computed Tomography (CT) image or Magnetic Resonance Image (MRI), along a longest axis in the image. Lymph nodes are measured along a short axis, which is perpendicular to the longest axis in the image slice. The RECIST guidelines call for computing the total disease burden on a patient as the sum of the long axis of the tumors and the short axis of the lymph nodes. The same target lesions are tracked at each treatment interval. Each treatment interval includes new measures and a new computed total disease burden.

The new computed total disease burden is compared with the minimal disease burden documented in the patient's treatment episode, which is called a "nadir," meaning lowest point. The nadir is the smallest total disease burden documented in the treatment episode. The percentage increase/decrease of the total disease burden relative to the nadir is used to classify the disease state, such as one of "respond," "stable," or "progress." "Respond" means the patient is improving. "Progress" means the tumors are increasing in size, which may mean the current treatment is ineffective. Because tumors and lymph nodes are measured differently, classification of a lesion as a tumor or a lymph node affects the computed total disease burden. Incorrect classification can lead to incorrect response assessments and untimely or unjust abortion of a treatment.

Categorization of the lesion as a tumor or a lymph node can be difficult from the CT or MR image. As a result, categorizing some target lesions are not clearly indicated solely from the image, and may be ambiguously reported in a radiology report. In addition, the lesion description in the report may also be ambiguous to the consumer that has no or limited clinical background. Where the categorization of the target lesion cannot be determined by the personnel tabulating lesion measurements, the measure is undetermined, e.g. whether to measure based on the short or long axis. With the measure undetermined, the classification of the disease and the disease burden are thus unknown or undetermined.

The following discloses a new and improved handling of undetermined quantifiable lesions which addresses the above-referenced issues, and others.

In accordance with one aspect, a lesion tracking system includes a data interface, a computation engine, and a visualization engine. The data interface is configured to receive an identification and measurements of at least one target lesion, which includes at least one undetermined target lesion according to a plurality of determined categories, and each undetermined target lesion is quantified differently according to each of the plurality of determined categories. The computation engine is configured to compute a range of quantified measurements according to each determined category for each undetermined target lesion, and to compute a quantified total range for the at least one target lesion based on a quantified measurement for each determined target lesion and the computed range for each of the at least one undetermined target lesion. The visualization engine is configured to generate a human readable display of the computed quantified total range for the at least one target lesion.

In accordance with another aspect, a method of lesion tracking includes receiving an identification and measurements of at least one target lesion, which includes at least one undetermined target lesion according to a plurality of determined categories, and each undetermined target lesion is quantified differently according to each of the plurality of determined categories. A range of quantified measurements is computed according to each determined category for each undetermined target lesion, and a quantified total range is computed for the at least one target lesion based on a quantified measurement for each determined target lesion and the computed range for each of the at least one undetermined target lesion. A human readable display of the computed quantified total range is generated for the at least one target lesion.

In accordance with another aspect, a lesion tracking system includes one or more processors configured to receive a long axis measurement and a short axis measurement for at least one target lesion, and the at least one target lesion includes at least one undetermined target lesion. The one or more processors are further configured to calculate a total disease burden range, which ranges from a first sum of a minimum of the received measurements for each of the at least one undetermined target lesion and the long axis measurement for each tumor of the at least one target lesion and the short axis measurement for each lymph node of the at least one target lesion, to a second sum of a maximum of the received measurements for each of the at least one undetermined target lesion and the long axis measurement for each tumor of the at least one target lesion and the short axis measurement for each lymph node of the at least one target lesion. The one or more processors are further configured to control a display device to display the calculated total disease burden range.

One advantage is an evaluation consistent with guidelines, which accommodates undetermined lesions.

Another advantage resides in alerting a healthcare practitioner of a needed determination of a category for an undetermined target lesion.

Another advantage resides in accommodating changes and ambiguity in lesion tracking.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
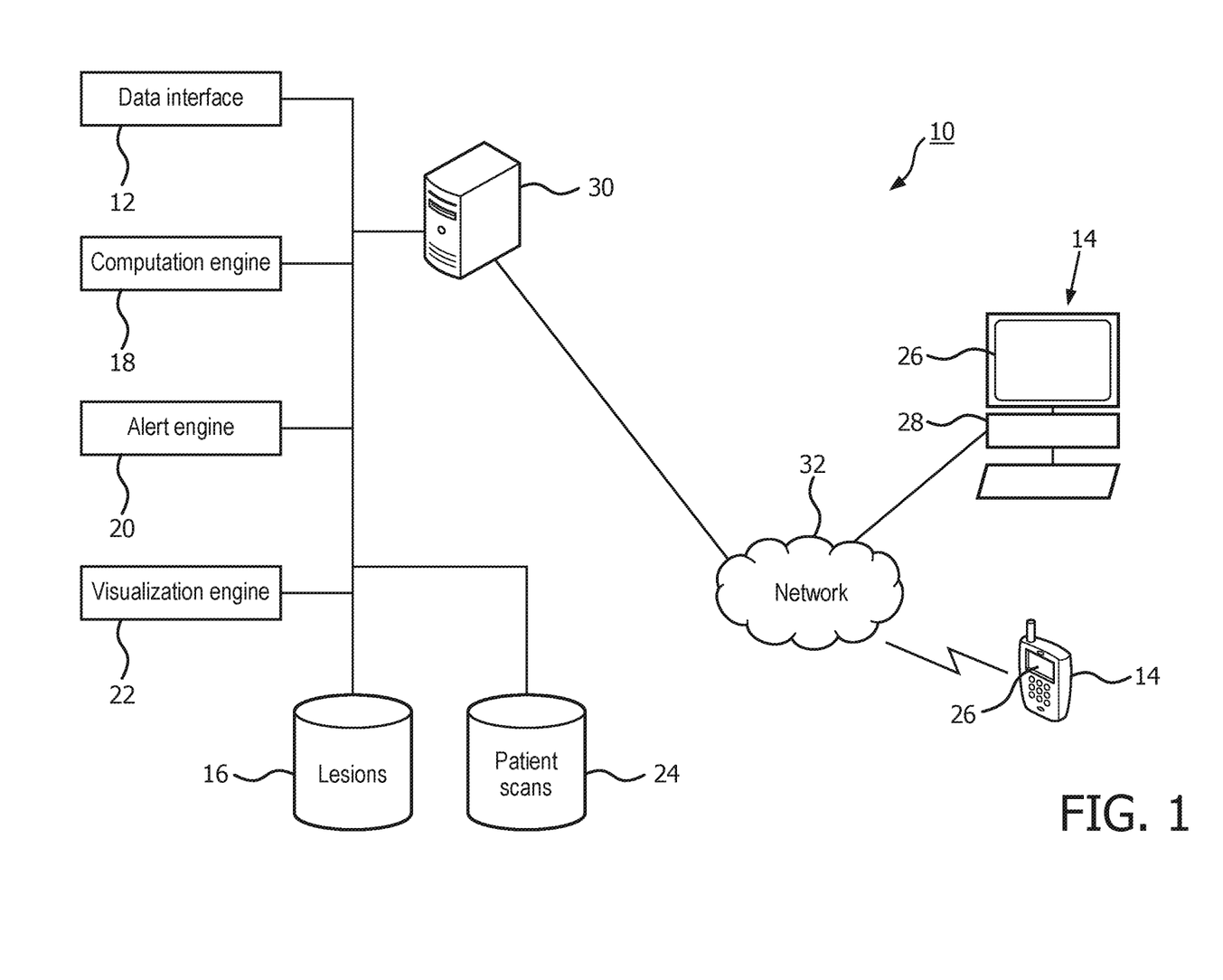
FIG. 1 diagrammatically illustrates an embodiment of a system for handling of undetermined quantifiable lesions.

With reference to FIG. 1, an embodiment of a longitudinal lesion tracking system 10 configured to handle quantifiable lesions is diagrammatically illustrated. The system includes a data interface, device, or means 12, which receives data that includes identification, measurements, and a category for each target lesion tracked. Exemplary data interface means include computing devices, such as a communicatively connected server, a desktop, a laptop, a handheld, a body mounted or worn computer processor, configured to receive data through touch, sound, motion and/or a communicative connection with other systems, and the like. The target lesions tracked can include determined targets lesions, e.g. a category identified for the target lesion, or undetermined target lesions, e.g. the category is specified as undetermined or unknown. The measurements include values which quantify the target lesion according to each category. For example, a tumor target lesion is quantified on a long axis in an image, and a lymph node target lesion is quantified on a short axis or axis perpendicular to the long axis in the image. The long axis measurement and the short axis measurement represent different quantified measurements as two determined categories. The image or measurements from the image can be received from a Picture Archiving and Communication System (PACS), Radiology Information System (RIS), Hospital Information System (HIS), and the like, or entered by a user. In other embodiments, additional categories are contemplated, each associated with a particular measurement or measurements, and at least two categories quantify the lesion differently. In another embodiment, a third category of lesions is determined based on an average of the long axis and the short axis. The data interface receives the data from a portable or stationary computing device or means 14, such as a desktop, laptop, tablet, smartphone, body mounted device, and the like and/or another system, such as the PACS, RIS, HIS, and the like. The data interface 12 receives data for each tracked lesion at a plurality of occurrences, where measurements of progress are made and/or at each treatment interval. For example, each time a patient is imaged and measurements taken, the data is received. The data interface 12 is configured to receive data for all lesions tracked, including non-target lesions. The data interface 12 stores the received data in a lesion data store 16.

A computer processor, computation engine or other computation unit, device, or means 18 computes a range of quantified measurements for each undetermined target lesion, based on possible outcomes according to each determined category. The computation unit 18 is configured to retrieve the data from the lesion data store 16 or receive the data directly from the data interface 12. The computation unit 18 computes a quantified total range, which includes a sum of the quantified measurement for each determined target lesion and the computed range for each undetermined target lesion. The computed range, in one embodiment, for each undetermined target lesion, is a minimum value from the set of values of the possible outcomes, and a maximum value for the set of values of the possible outcomes. The computation unit 18 computes the quantified total range for each occurrence. The computation unit 18 computes a nadir range of values, which is a lowest quantified total range over the occurrences. The computation unit 18 computes a response range indicative of the disease state, which includes a change between the total nadir range and the computed quantified total range. For example, given a single undetermined lesion with two measurements, a total nadir range of 12.1-14.2 mm, and a computed quantified total range of 13.6-15.1 mm, the response range is 6.3-12.4%, which represents a 6.3% increase, with respect to the first measurement corresponding to a first determined category, and a 12.4% increase, with respect to the second measurement corresponding to a second determined category.

An alert engine, unit, device, or means 20 constructs an alert to one or more of the computing devices, such as the computing device 14. The alert alerts a healthcare practitioner of a change in disease state for the response range, which includes a change, increase or decrease, in measurements of at least one undetermined target lesion contributing to the change in disease state. For example, an alert includes a text and/or graphic message constructed with two categories of determined lesions, two determined target lesions which are unchanged from the nadir values, and one undetermined target lesion which increases from the nadir range in at least one measurement to change disease state, e.g. to "progress," based on one of the measurements corresponding to a determined category. For example, of the two measurements for the undetermined target lesion, at least one increases sufficiently in the measurement to change the disease state. The alert unit 20 can include a notice in the alert which identifies the undetermined lesion or lesions contributing to the change in disease state. The notice can include the category or measurement indicative of the change in disease state. The alert can include notice that a determination of the undetermined lesion is to be resolved, e.g. category determined for the undetermined lesion. For example, an undetermined target lesion grows from one occurrence to the next, such that the response range exceeds a threshold value of 20%, which classifies the disease state as "progress," while the other tracked lesions do not change in size. In the example, the undetermined target lesion grows only in one measurement sufficiently to change the disease state. In another example, a determined target lesion grows sufficiently to change the disease state, while measurements of an undetermined lesion remain constant. In the former example, an alert identifies the undetermined lesion and corresponding category, which indicates the change in disease state. In the latter example, the undetermined lesion can remain unresolved, e.g. category remains specified as undetermined. The alarm may include audio components.

A visualization engine, unit, device, or means 22 visualizes the computed quantified total range for the at least one target lesion. The visualization unit 22 is configured to visualize the identity of each target lesion, the measurements of each lesion for the occurrences, and/or the computed response range. The visualization unit 22 is configured to visualize the measurements and computed values for one or more occurrences. The visualization unit 22 is configured to display images and/or links to images in the visualization from a patient scan data store 24, which correspond to the occurrence and target lesion. The visualized quantified total range, the identity of each target lesion, the measurements, the computed nadir range, and/or the computed response range, are displayed on a display device 26, such as a workstation display, mobile computer display, body mounted or worn display, etc., of the computing device 14.

The various engines, units, means, or interfaces 12, 18, 20, 22 are suitably embodied by one or more data processing device, such as an electronic processor or electronic processing device 28 of the computing device 14, or by a network-based server computer 30, operatively connected with the computing device 18 by a network 32, or so forth. The various units, means, or interfaces can be implemented as Web-based, e.g. HTML, XML, etc., using a hypertext transfer protocol (HTTP) supported computer server. Moreover, the disclosed computation, alert, and visualization techniques are suitably implemented using a non-transitory storage medium storing instructions (e.g., software) readable by a data processing device and executable by the data processing device to perform the computation, alert, and visualization techniques.

The data stores 16, 24 are suitably embodied by computer memory, which can include file structures, database structures including relational and/or object-based, local or cloud storage, storage media including random access disk, solid state disk, removable storage, and the like. The visualization unit or means 22 can be embodied by a processor configured to control a display device, such as a computer monitor, a television screen, a touch screen, tactile electronic display, braille screen, cathode ray tube (CRT), storage tube, bistable display, electronic paper, vector display, flat panel display, vacuum fluorescent display (VF), light-emitting diode (LED) displays, electroluminescent display (ELD), plasma display panels (PDP), liquid crystal display (LCD), organic light-emitting diode displays (OLED), a projector, and Head-mounted display, and the like.

Figure 2:
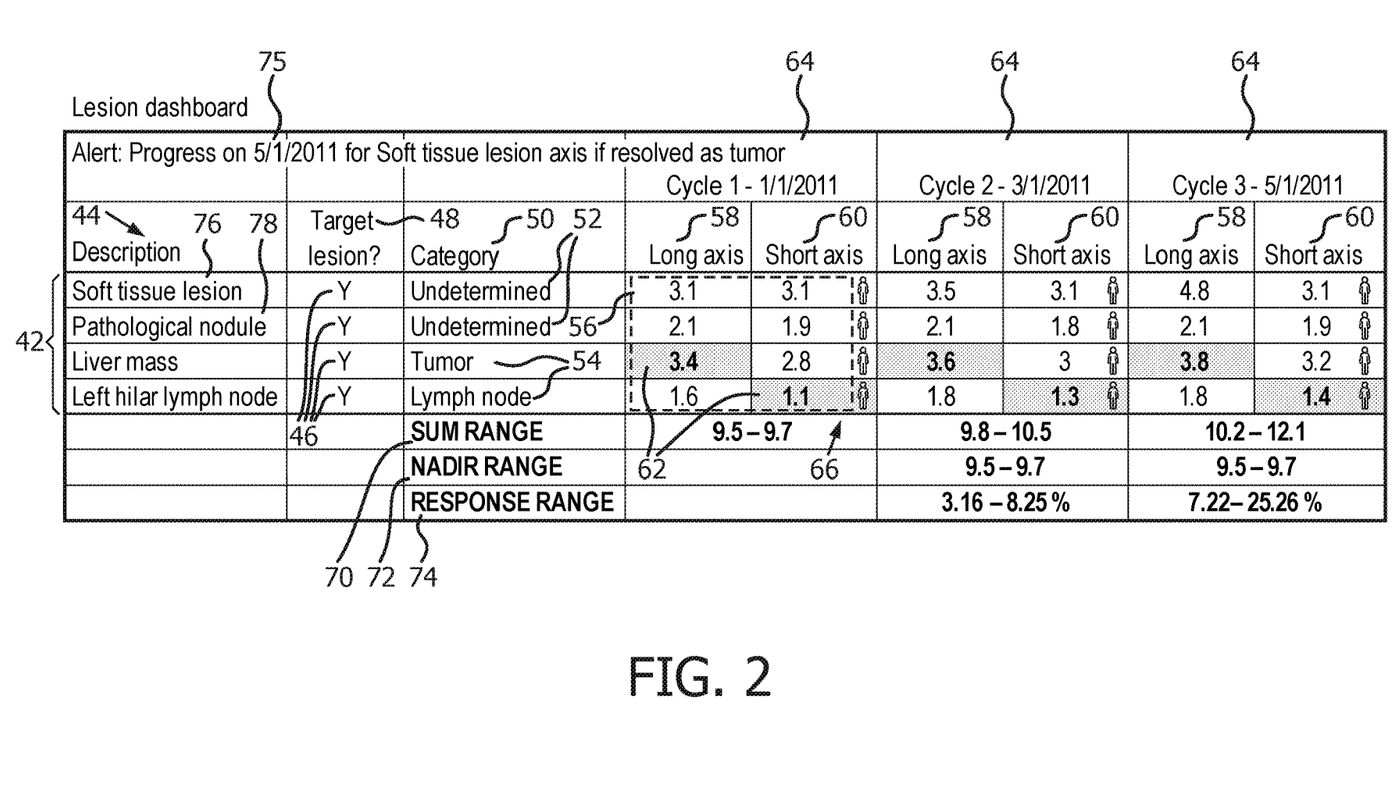
FIG. 2 illustrates an exemplary visualized display of undetermined quantifiable lesions.

With reference to FIG. 2, an exemplary visualized display 40 of the undetermined quantifiable lesions is illustrated. The display can be interactive, which includes both data entry and/or display. The interactive display can include data entry aids, such as drop down boxes, radio buttons, and the like. The display 40 includes lesions 42, which include an identification or description 44. The lesions 42 can include non-target lesions. Each target lesion 46 is identified in the visualized display 40 by a type indicator 48, e.g. target lesion="Y" (yes), non-target lesion="N" (no) or blank. Each target lesion 46 includes a category 50, which is either undetermined 52, or one of a determined 54 category, such as tumor, lymph node, etc. The visualized display 40 includes measurements 56, which include a long axis measurement 58 and a short axis measurement 60. For determined target lesions 54, the quantified measurement 62 is identified. For example, a tumor target lesion is quantified based on the long axis measurement of 3.4 mm, and a lymph node is quantified based on the short axis measurement of 1.1 mm.

The visualized display 40 includes occurrences 64, which are points in time where measurements were taken of the lesions. In the exemplary display, three occurrences are visualized. Additional occurrences can be visualized by, for example, scroll bars added to extend the visualized display longitudinally, e.g. scroll horizontally.

The visualized display 40 includes icons 66, which represent links to images in the patient scans data store 24 corresponding to the image from which the measurement is taken. For example, selecting an icon according to row and column of the target lesion and the occurrence displays the image of the lesion imaged or scanned at the time of the occurrence or treatment. Selecting the link can include focusing the image display on the corresponding lesion in a display overlay, such as a splash screen, or in a separate window display, highlighting the lesion in the image, indicating measurement points, and the like.

The visualized display 40 includes the quantified total range 70, the nadir range 72, and the response range 74. The quantified total range 70 includes the quantified measurement 62 for each determined target lesion 54. The tumor is quantified at 3.4 in the long axis, and the lymph node is quantified at 1.1 in the short axis, for a total of 4.5. The quantified total range 70 includes the range for each undetermined target lesion 52. The range of values in the first occurrence across the long axis measurement 58 and short axis measurement 60 of a first undetermined target lesion 76 is 3.1–3.1. The range of values in the first occurrence across the long axis measurement 58 and short axis measurement 60 of a second undetermined target lesion 78 is 1.9–2.1. The total range of undetermined target lesions 52 is 3.1+1.9 to 3.1+2.1 or 5.0–5.2. Summing the determined and undetermined values yields a quantified total range of 4.5+5.0 or 9.5 to 4.5+5.2 or 9.7, e.g. 9.5-9.7. The quantified total range 70 is computed for each occurrence 64, according to the measurements 56, by lesion received for the occurrence 64.

The nadir range 72 is computed as a minimum of the quantified total range over the occurrences 64. For example, with tracked lesions which remain stable or progress, the nadir will likely be the quantified total range of the first occurrence. If the tracked lesions respond to treatment, a nadir of a later occurrence is possible. The nadir range 72 is computed or re-computed after each occurrence 64.

The response range 74 is computed at each occurrence 64, which represents a change in target lesions from the nadir values of prior occurrences. In the exemplary display, the quantified total range of the first occurrence is 9.5–9.7. The quantified total range of the second occurrence is 9.8–10.5, which is an increase of 3.16–8.25% over the nadir values, which are, in this instance, the quantified total range of the first occurrence. In the third occurrence, an undetermined lesion described as "Soft tissue lesion," increases in the long axis to 4.8, which contributes to a response range greater than a threshold value of 20%, indicative of a change in disease state from "stable" to "progress."

An alert 75 can be constructed based on the change in disease state. The alert 75, such as a text and/or graphical message, a splash screen, or highlighted text and numbers, indicates the change in disease state. The alert 75 can include the identity of the undetermined target lesion, e.g. "Soft tissue lesion" description; the quantified measurement, e.g. the long axis measurement of 4.8; and the possible category which as resolved contributes to the change in disease state, e.g. tumor.

In another embodiment, the visualized display includes the measurements shown graphically, such as a line graph, a bar graph, and the like. The graph can include designation of determined lesions and undetermined lesions delineated separately, and/or the undetermined lesions indicated as a margin of error. The graph can be expressed as a timeline of the occurrences. The thresholds for changes in disease state can be visually indicated, such as a dotted line, colored area, etc.

With reference to FIGS. 3A-3D, exemplary computations of undetermined quantifiable lesions according to one embodiment are illustrated. In one embodiment, the computations can be visualized, such as shown. The exemplary computations illustrate the possible outcomes for resolving the undetermined target lesions, as described with reference to FIG. 2. The computed possible outcomes are represented as T where X is the number of categories for determined target lesions, and n is the number of undetermined target lesions. For example, with determined categories of tumor and lymph node, X=2, and with 2 underdetermined lesions, n=2, which gives $2^2$ or 4 possible outcomes or resolutions, which are depicted in FIGS. 3A-3D, based on the example of FIG. 2D.

Figure 3A:
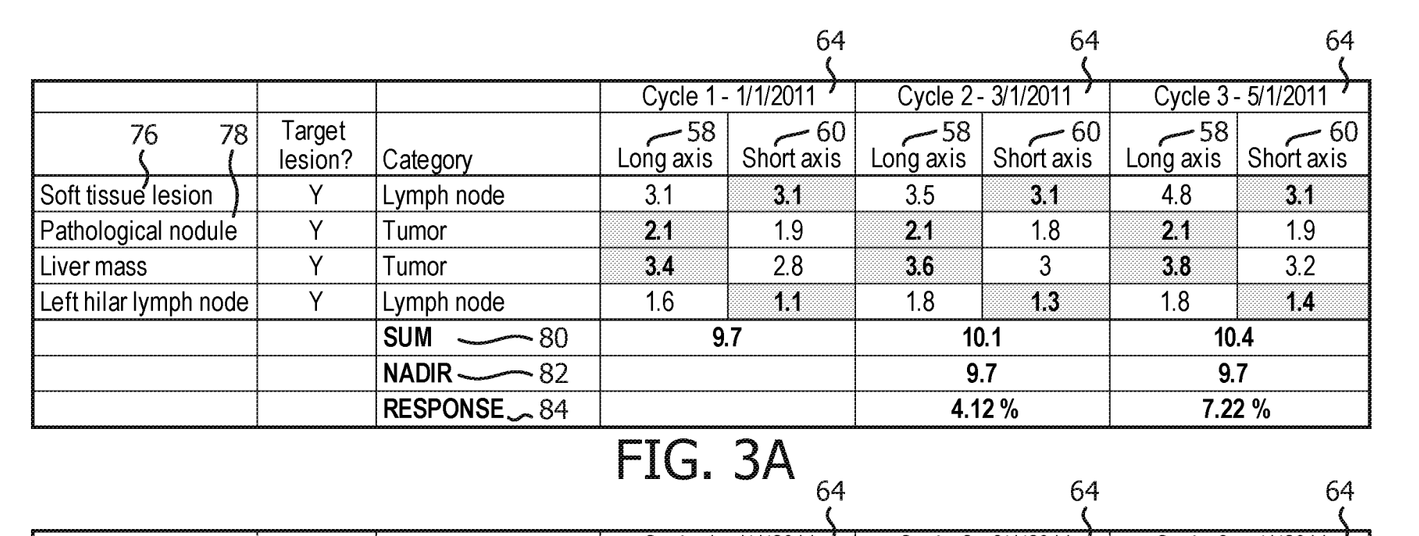
FIGS. 3A-3D illustrate exemplary computations of undetermined quantifiable lesions according to one embodiment.

FIG. 3A depicts the first undetermined target lesion 76 of FIG. 2 resolved as a lymph node, i.e. determined category of lymph node, and the second undetermined target lesion 78 resolved as a tumor, i.e. determined category of tumor. With the resolved target lesions, the first resolved target lesion as a lymph node is quantified, based on the short axis measurement 60 or a constant 3.1 mm over the three occurrences. The second resolved target lesion as a tumor is quantified, based on the long axis measurement 58 or a constant 2.1 mm across the three occurrences. The ranges of the quantified total range 70, the nadir range 72, and the response range 74 of FIG. 2 are resolved to single values as quantified sums 80, nadirs 82, and responses 84. The responses 84 of 4.12% in the second occurrence, and 7.22% in the third occurrence over the nadir 82, are due to the increase of the two determined target lesions of the liver mass and the left hilar lymph node. The responses 84 are less than the threshold value for the change in disease state, such as less than 20%, and do not generate the alert.

Figure 3B:
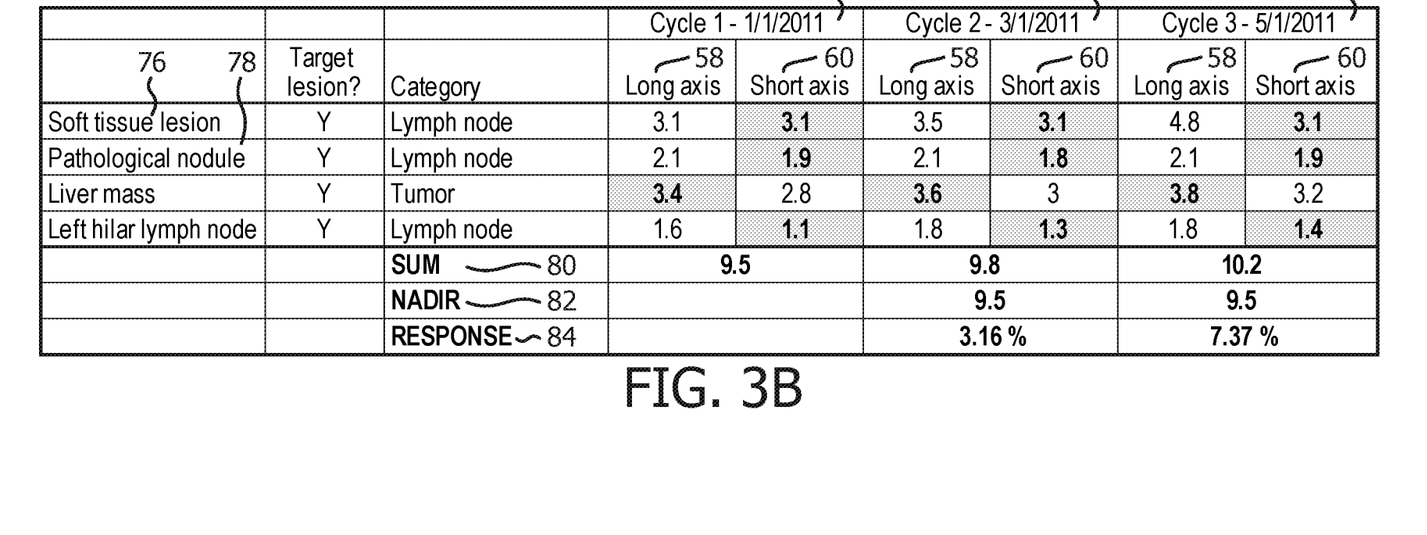

FIG. 3B depicts the first undetermined target lesion 76 and the second undetermined target lesion 78 resolved as lymph nodes. Both resolved lymph node target lesions are quantified based on the short axis measurement 60. The responses 84 are less than the threshold for the change in disease state and do not generate the alert.

Figure 3C:
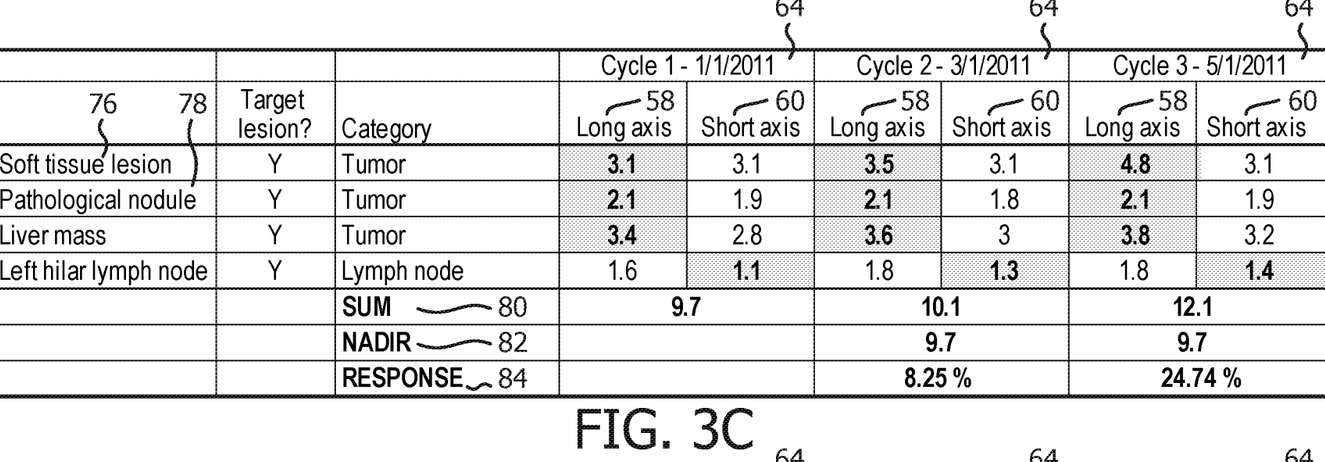

FIG. 3C depicts the first undetermined target lesion 76 and the second undetermined target lesion 78 resolved with the determined category of tumor. Tumors are quantified based on the long axis measurement 58. The response 84 in the third occurrence 64 of 24.74%) exceeds a threshold value of 20%, for a change in disease state from "stable" to "progress." The change in disease state causes the alert 75 to be generated.

Figure 3D:
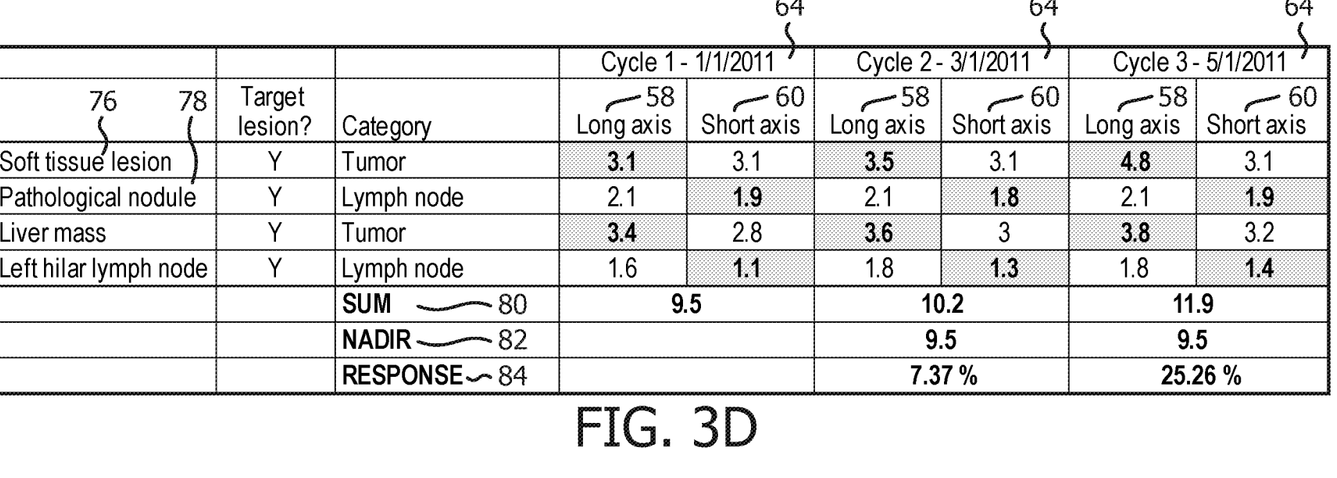

FIG. 3D depicts the first undetermined target lesion 76 resolved as a tumor and the second undetermined target lesion 78 resolved as a lymph node. The response 84 in the third occurrence 64 exceeds the threshold of a change in disease state, and the alert is generated. The first undetermined target lesion contributes to the change in disease state, e.g. changing the possible category from tumor to lymph node, independent of the other undetermined target lesion, reduces the response 84 to less than the threshold value. One or more undetermined target lesions can be identified as contributing to the change in disease, which indicates that the contributing undetermined target lesions are to be resolved, e.g. that a category is actually determined by some means.

In one embodiment, the exemplary visualized displays depicted in FIGS. 3A-3D can be utilized to drill down on the exemplary display of FIG. 2. For example, a selection of a response range and/or undetermined lesion(s) can return one or more displays or portions of displays, as indicated in FIGS. 3A-3D, such as the impact of the selected undetermined target lesions on the sum or quantified total disease burden, the nadir, and/or the responses.

Figure 4:
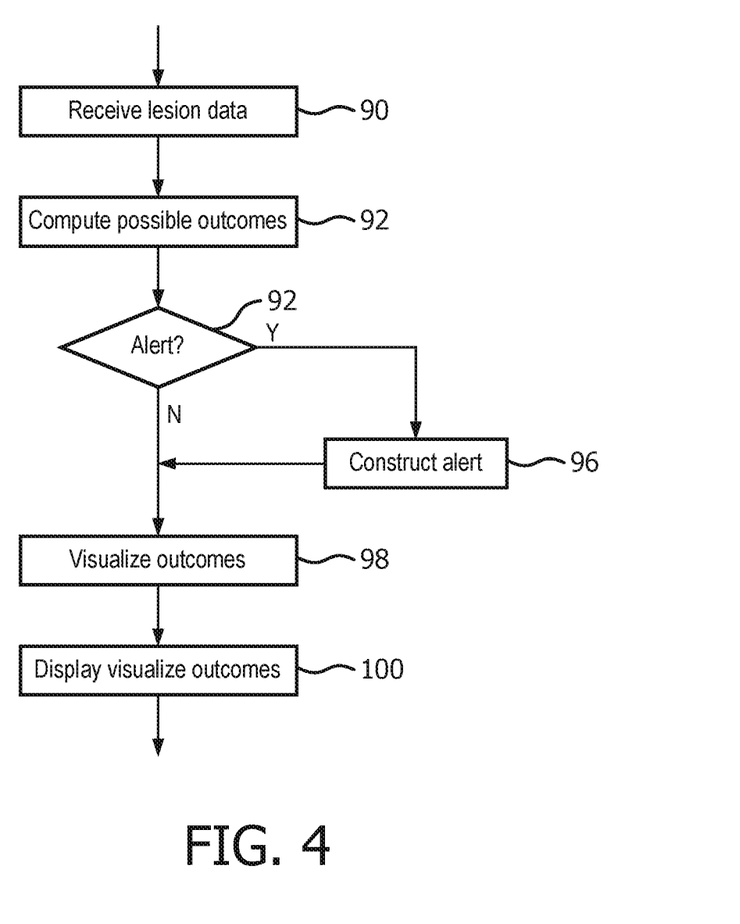
FIG. 4 flowcharts one method of an embodiment of handling undetermined quantifiable lesions.

With reference to FIG. 4, one method of an embodiment of handling undetermined quantifiable lesions is flowcharted. In a step or by a module 90, lesion data is received. The lesion data includes one or more undetermined target lesions. The lesion data can include target and non-target lesions. The lesion data includes designation of target lesions, either by placement, e.g. entered or received in a particular manner, or by actual designation, e.g. the type indicator 48 entered or received. The lesion data is received either by user entry and/or by electronic transmission from one or more systems. The lesion data includes, for each lesion, the description of the lesion and the measurements. The measurements are received for each occurrence 64. The measurements include at least two measurements, which are quantified differently for the target lesion based on the determined category. For received target lesions which are determined, the category is received. For received target lesions which are undetermined, a category of undetermined is received, e.g. null value or some indicator representing undetermined. The lesion data can include further descriptive information of lesion, such as organ and/or physical location, and the like, or reference information, such as the corresponding image where the lesion is measured, biopsy status, and the like. The lesion data is received for each occurrence 64. The lesion data can be received continuously, intermittently, e.g. as available, or accumulated, e.g. as a batch. The lesion data includes a patient or subject identifier, or other identifier, to group the tracked lesions for computing the quantified total ranges, the nadir ranges, and the response ranges. The received lesion data is stored in the lesion data store 16.

The possible outcomes are computed in a step or by a module 92. The possible outcomes include the combinations for the undetermined target lesions, according to each possible determined category. For each combination or possible category, the measurement for the undetermined target lesion is quantified. For each determined target lesion, the measurement is quantified across the combinations. The step or module includes computing the quantified total range, the nadir range, and the response range across the combinations, e.g. the minimum and maximum quantified measurements across the combinations. The step includes computing the ranges for the received occurrences. For the first occurrence, the nadir range is set to the quantified total range, and the response range is not applicable. At subsequent occurrences, the nadir range is the minimum of the set of quantified total ranges prior to the most current quantified total range, and the response range is computed as the change from the nadir range. The response range can be expressed in absolute measurement values, e.g. values according to the scale of measurements and/or as a percentage value.

The call for an alert can be evaluated in a decision step or by a module 94. The response range is compared to predetermined threshold values for a change in disease state. The disease state can include any number of states and/or threshold values. For example, a disease state can include five categories, such as significant response, respond, stable, stable with growth, or progress, each state delineated with threshold values. In another example, the threshold value for a change in state from stable to progress is 18%. In a step or by a module 96, the alert is constructed based on the decision step evaluation. The alert is expressed as a message, such as a text message or email, or expressed as part of the visualized display of outcomes.

A human readable display is generated of the computed outcomes in a step or by a module 98. The visualized outcomes can be a textual display, as illustrated in FIG. 2 and FIGS. 3A-3D. The visualized outcomes can be a graphical display, such as a line graph, bar chart, etc. The visualized display includes the tracked lesions and the measurements for at least one occurrence. The visualized display includes the quantified total ranges 70, the nadir range(s) 72, and the response range(s) 74. The visualized display can include the disease state and/or constructed alerts. In a step or by a module 100, the visual outcomes are displayed on the display device 26.

The foregoing steps 90-96 can be performed by one or more computer processors or computation units, such as the interface and units 12, 18, 20, and 22. The steps 98 and 100 can be performed by the computing device 14 configured to control the display It is to be appreciated that in connection with the particular illustrative embodiments presented herein, certain structural and/or functional features are described as being incorporated in defined elements and/or components. However, it is contemplated that these features may, to the same or similar benefit, likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may, under suitable circumstances, be stand-alone elements or otherwise divided. Similarly, a plurality of particular functions described as being carried out by one particular element may be carried out by a plurality of distinct elements acting independently to carry out individual functions. Also, certain individual functions may be split up and carried out by a plurality of distinct elements acting in concert. Alternately, some elements or components, otherwise described and/or shown herein as distinct from one another, may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A lesion tracking system, comprising:
    a data interface configured to receive an identification and quantified measurements of each of a plurality of target lesions, the plurality of target lesions including at least one undetermined target lesion according to a plurality of determined categories and at least one determined target lesion whose category has been determined, wherein the quantified measurement of each of the at least one determined target lesions is determined by the determined category for that determined target lesion, and wherein each of the at least one undetermined target lesion is quantified according to each of the plurality of determined categories such that the quantified measurements for each undetermined target lesion comprise a long axis measurement and a short axis measurement;
    a computation engine configured to compute a quantified total range for the plurality of target lesions ranging from:
    a sum of the quantified measurement for each of the at least one determined target lesion and, for each of the at least one undetermined target lesion, a minimum of the quantified measurements according to each of the plurality of determined categories, to:
    a sum of the quantified measurement for each of the at least one determined target lesion and, for each of the at least one undetermined target lesion, a maximum of the quantified measurements according to each of the plurality of determined categories;
    a visualization engine configured to generate a human readable display of the computed quantified total range for the plurality of target lesions; and
    a display device configured to display the human readable display, wherein the human readable display comprises at least one of: (1) a textual display which includes the identification and the quantified measurements for each of the plurality of target lesions and the quantified total range, a nadir range, and a response range; and (2) a graphical display which includes the quantified total range, the nadir range, and the response range.

2. The lesion tracking system according to claim 1, wherein the data interface receives the quantified measurements by occurrence which are points in time where measurements were taken, for each of the plurality of target lesions; and
    wherein the computation engine computes the quantified total range for the plurality of target lesions for each occurrence.

3. The lesion tracking system according to claim 1, wherein the categories include a first category which is quantified based on the long axis measurement and a second category which is quantified based on the short axis measurement.

4. The lesion tracking system according to claim 1, wherein the computation engine is further configured to:
    compute the nadir range for the plurality of target lesions; and
    compute the response range indicative of a disease state which includes a change between the computed nadir range and the computed quantified total range.

5. The lesion tracking system according to claim 1, further including:
    an alert engine configured to construct an alert when the response range is associated with a change in disease state.

6. The lesion tracking system according to claim 5, wherein the alert includes a notice and the identification of at least one of the at least one undetermined target lesion; and a corresponding measurement for at least one of the plurality of determined categories indicative of a change in disease state.

7. The lesion tracking system according to claim 5, wherein the alert includes a message with a hyperlink to at least one of:
- the lesion tracking system;
- at least one image of the at least one undetermined target lesion; and
- a program which resolves the undetermined category.

8. The lesion tracking system according to claim 1, wherein the quantified measurements of each of a plurality of target lesions received by the data interface comprise quantified measurements for each of the plurality of target lesions according to a plurality of occurrences, which are points in time where measurements were taken of the plurality of target lesions; and wherein the computation engine computes the quantified total range for the plurality of target lesions for each of the plurality of occurrences, and the nadir range and the response range based on the computed quantified total range which includes the at least one undetermined target lesion.

9. A method of lesion tracking, comprising:
- receiving an identification and quantified measurements of each of a plurality of target lesions, the plurality of target lesions including at least one undetermined target lesion according to a plurality of determined categories, and at least one determined target lesion whose category has been determined, wherein the quantified measurement of each of the at least one determined target lesions is determined by the determined category for that determined target lesion, and wherein each of the at least one undetermined target lesion is quantified according to each of the plurality of determined categories to create a set of quantified measurements comprising a long axis measurement and a short axis measurement;
- computing a quantified total range for the plurality of target lesions ranging from:
- a sum of the quantified measurement for each of the at least one determined target lesion and, for each of the at least one undetermined target lesion, a minimum of a set of the quantified measurements according to each of the plurality of determined categories, to:
- a sum of the quantified measurement for each of the at least one determined target lesion and, for each of the at least one undetermined target lesion, a maximum of a set of the quantified measurements according to each of the plurality of determined categories; and
- generating a human readable display of the computed quantified total range for the plurality of target lesions.

10. The method of lesion tracking according to claim 9, wherein the categories include a first category which is quantified based on the long axis measurement and a second category which is quantified based on the short axis measurement.

11. A non-transitory computer-readable storage medium carrying software characterized in that it is configured to control one or more data processing devices to perform the method according to claim 9.

* * * * *